United States Patent
Dace

(10) Patent No.: US 10,449,006 B2
(45) Date of Patent: Oct. 22, 2019

(54) SURGICAL INSTRUMENT AND METHOD

(71) Applicant: Warsaw Orthopedic, Inc, Warsaw, IN (US)

(72) Inventor: Mark C. Dace, Collierville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 5 days.

(21) Appl. No.: 15/480,153

(22) Filed: Apr. 5, 2017

(65) Prior Publication Data

US 2018/0289426 A1    Oct. 11, 2018

(51) Int. Cl.
*A61B 17/70*   (2006.01)
*A61B 34/20*   (2016.01)
*A61B 17/88*   (2006.01)
*A61B 17/56*   (2006.01)
*A61B 90/00*   (2016.01)
*A61B 90/50*   (2016.01)

(52) U.S. Cl.
CPC .......... *A61B 34/20* (2016.02); *A61B 17/7011* (2013.01); *A61B 17/8863* (2013.01); *A61B 2017/564* (2013.01); *A61B 2034/2051* (2016.02); *A61B 2034/2055* (2016.02); *A61B 2090/372* (2016.02); *A61B 2090/3762* (2016.02); *A61B 2090/3966* (2016.02); *A61B 2090/3983* (2016.02); *A61B 2090/502* (2016.02)

(58) Field of Classification Search
CPC .................................. A61B 17/7074–17/7091
See application file for complete search history.

(56) References Cited

U.S. PATENT DOCUMENTS

| | | | |
|---|---|---|---|
| 5,595,193 A | 1/1997 | Walus et al. | |
| 6,021,343 A * | 2/2000 | Foley ..................... | A61B 17/16 600/417 |
| 6,226,548 B1 * | 5/2001 | Foley .................. | A61B 17/7083 600/426 |
| 6,348,058 B1 * | 2/2002 | Melkent ............. | A61B 17/1757 600/429 |
| 6,351,659 B1 * | 2/2002 | Vilsmeier ................ | A61B 6/12 600/407 |
| 6,381,485 B1 * | 4/2002 | Hunter .................. | G06T 3/0068 324/244 |
| 6,551,325 B2 * | 4/2003 | Neubauer ............ | A61B 17/154 606/87 |
| 6,980,849 B2 * | 12/2005 | Sasso ................... | A61B 17/863 378/20 |
| 7,660,623 B2 | 2/2010 | Hunter et al. | |
| 7,881,770 B2 * | 2/2011 | Melkent ................... | A61B 5/06 600/424 |
| 7,998,062 B2 | 8/2011 | Gilboa | |
| 8,105,339 B2 | 1/2012 | Melkent et al. | |
| 8,167,823 B2 | 5/2012 | Nyez et al. | |
| 8,467,851 B2 * | 6/2013 | Mire ...................... | A61B 34/20 600/407 |

(Continued)

*Primary Examiner* — Eduardo C Robert
*Assistant Examiner* — Michelle C Eckman

(57) ABSTRACT

A surgical instrument comprises a member connected with a spinal implant defining an axis. A first image guide is connected with the member and oriented relative to a sensor to communicate a signal representative of a position of the member. A second image guide is connected with the member and oriented to represent an angle measuring a second orientation of the axis relative to a first orientation. Systems, implants and methods are disclosed.

20 Claims, 4 Drawing Sheets

(56) References Cited

U.S. PATENT DOCUMENTS

| | | | |
|---|---|---|---|
| 8,696,685 B2 | 4/2014 | Gilboa | |
| 8,801,601 B2 | 8/2014 | Prisco et al. | |
| 9,510,771 B1* | 12/2016 | Finley | A61B 5/743 |
| 9,833,267 B2* | 12/2017 | King | A61B 17/708 |
| 2004/0158260 A1* | 8/2004 | Blau | A61B 17/7083 |
| | | | 606/108 |
| 2005/0021037 A1 | 1/2005 | McCombs et al. | |
| 2005/0027832 A1 | 2/2005 | Bavaria et al. | |
| 2005/0085714 A1* | 4/2005 | Foley | A61B 17/1735 |
| | | | 600/424 |
| 2009/0187194 A1* | 7/2009 | Hamada | A61B 17/7001 |
| | | | 606/104 |
| 2009/0326586 A1* | 12/2009 | Duarte | A61B 17/7089 |
| | | | 606/264 |
| 2010/0036384 A1* | 2/2010 | Gorek | A61B 17/7091 |
| | | | 606/104 |
| 2011/0218546 A1* | 9/2011 | De la Fuente Klein | A61B 17/155 |
| | | | 606/104 |
| 2013/0261609 A1* | 10/2013 | Dicorleto | A61B 17/1622 |
| | | | 606/1 |
| 2014/0100616 A1* | 4/2014 | Shipp | A61B 17/7082 |
| | | | 606/86 A |
| 2014/0277198 A1* | 9/2014 | Stad | A61B 17/7074 |
| | | | 606/86 A |
| 2014/0316420 A1* | 10/2014 | Ballard | A61B 17/7002 |
| | | | 606/102 |
| 2015/0105833 A1* | 4/2015 | Simpson | A61B 5/06 |
| | | | 606/86 R |
| 2015/0305786 A1* | 10/2015 | Wehrle | A61B 90/98 |
| | | | 606/86 A |
| 2016/0081818 A1* | 3/2016 | Waugh | A61B 17/0206 |
| | | | 623/17.16 |
| 2016/0089188 A1* | 3/2016 | McBride, Jr. | A61B 17/7076 |
| | | | 606/279 |
| 2017/0095240 A9* | 4/2017 | Waugh | A61B 17/025 |
| 2017/0258535 A1* | 9/2017 | Crawford | A61B 17/025 |
| 2017/0273677 A1* | 9/2017 | Gorek | A61B 17/7082 |
| 2017/0340367 A1* | 11/2017 | Beger | A61B 17/7083 |
| 2017/0348061 A1* | 12/2017 | Joshi | A61B 5/066 |
| 2017/0360515 A1* | 12/2017 | Kozak | A61B 34/20 |
| 2018/0008253 A1* | 1/2018 | Thommen | A61B 17/025 |
| 2018/0055546 A1* | 3/2018 | Beger | A61B 17/7083 |

* cited by examiner

US 10,449,006 B2

SURGICAL INSTRUMENT AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, corpectomy, discectomy, laminectomy and implantable prosthetics. For example, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior technologies.

SUMMARY

In one embodiment, a surgical instrument is provided. The surgical instrument comprises a member connectable with a head of a bone fastener having a shaft attachable with tissue. The member is movable with the head to identify a range of movement of the head relative to the shaft. An image guide is connected with the member and oriented relative to a sensor to communicate a signal representative of the range of movement. In some embodiments, surgical systems, implants, spinal constructs and methods are provided.

In one embodiment, a method for treating a spine is provided. The method comprising the steps of: engaging a surgical instrument with a head of at least one bone fastener having a shaft attached with tissue; and moving the surgical instrument with the head to identify a range of movement of the head relative to the shaft, the surgical instrument including an image guide oriented relative to a sensor to communicate a signal representative of the range of movement.

In one embodiment, a surgical system is provided. The surgical system comprises at least one bone fastener including a head and a shaft attachable with tissue. The head includes a selected movement configuration relative to the shaft. A surgical instrument is connectable with the head and is movable with the head to identify a range of movement of the head relative to the shaft. The surgical instrument includes an image guide oriented relative to a sensor to communicate a signal representative of the range of movement. A tracking device includes the sensor that receives the signal and communicates with a processor to generate data for display of an image from a monitor. The image represents position of the at least one bone fastener relative to the tissue.

BRIEF DESCRIPTION OF THE DRAWINGS

The present disclosure will become more readily apparent from the specific description accompanied by the following drawings, in which.

DETAILED DESCRIPTION

Figure 1:
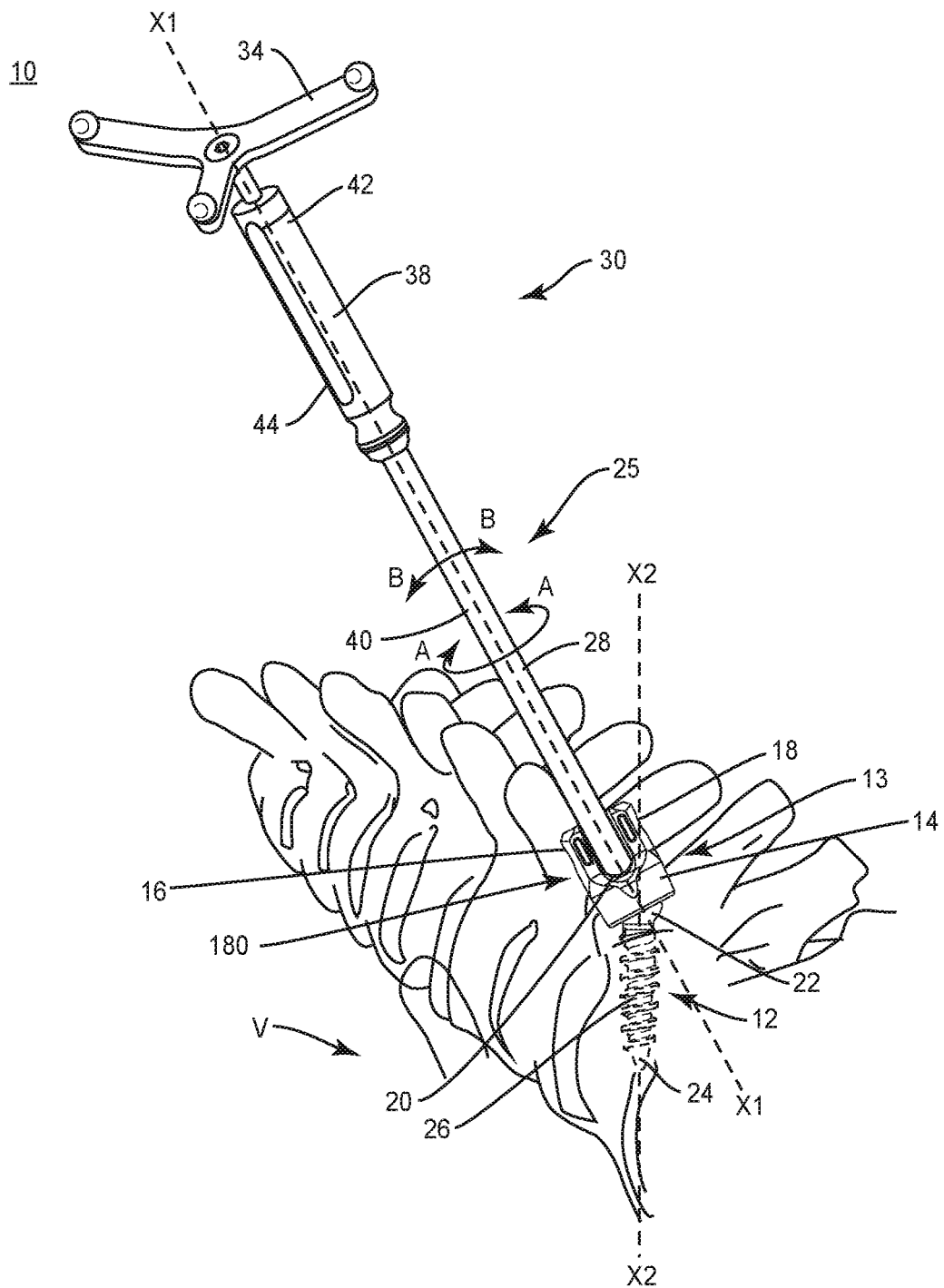
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system for preparing a surgical site, and a method for treating a spine. In some embodiments, the surgical system includes a surgical instrument having an image guide oriented relative to a sensor to communicate a signal representative of a range of movement of a receiver of a bone fastener. In some embodiments, the surgical system includes a surgical navigation system and/or an automated rod bending device.

In some embodiments, the present surgical system includes a surgical instrument that identifies screw head impingement recognition with surgical navigation, which can provide rod bending optimization. In some embodiments, the present surgical system is employed with a method for posterior fusion rod bending. In some embodiments, the present surgical system is employed with a method such that a navigation system identifies individual screw head data points located in three dimensional space and a processor interpolates and displays an image between these points to form a shape of a spinal rod. In some embodiments, the method includes identifying flexibility of one or more receivers or tulip heads of bone fasteners. In some embodiments, the implanted flexibility in the receivers is based on the design of the receiver and the proximity of an outer boundary of the receiver to a patient's bony anatomy. For example, when the receiver contacts the bony anatomy, the potential flexibility is reduced due to the impingement.

In some embodiments, the present surgical system includes a surgical instrument employed with a method of using a navigation system to measure the actual receiver angular displacement by allowing a surgeon to perform a circular sweeping motion of the navigated surgical instrument and recording the allowable displacement of the receiver per the bony impingement points. For example, the identified true angular allowance can be used to optimize a rod bending software model and eliminate unnecessary contouring and/or weakening of fixation rods.

In some embodiments, the present surgical system includes a surgical instrument employed with a method used to measure the actual flexibility of a screw head after insertion into a pedicle. In some embodiments, the present surgical system provides data signals that are then delivered to an automated rod bending device for optimized rod shaping. In some embodiments, the present surgical system provides actual flexibility of each screw head to optimize a fixation rod path between screws during automated rod bending. In some embodiments, the present surgical system identifies impingement of the screw on the bony anatomy to avoid restriction on receiver flexibility.

In some embodiments, the present surgical system includes a surgical instrument that has an instrument tracker and a distal/working end. In some embodiments, the surgical tracker provides indicia and/or display of a location and angulation of the surgical instrument and its distal/working end. In some embodiments, the surgical system includes a surgical instrument having one or more image guides, which include one or more fiducial markers. In some embodiments, the fiducial marker includes a single ball-shaped marker. In some embodiments, the image guide is disposed adjacent a proximal end of the surgical instrument. In some embodiments, the image guide provides indicia and/or display of a precise rotational and/or linear position of the image guide on the surgical instrument. In some embodiments, this configuration provides indicia and/or display of an amount of manipulation, movement, translation and/or rotation of the implant with tissue.

In some embodiments, the surgical system includes a surgical instrument having one or more image guides, which include a tracker that provides location of a surgical instrument in three dimensions, and a tracker that provides location of the surgical instrument and/or a spinal implant in two dimensions, such as, for example, a selected plane. In some embodiments, this configuration provides indicia and/or display of implant position corresponding to an amount of manipulation, movement, translation and/or rotation of the implant with tissue.

In some embodiments, the surgical system comprises a navigation compatible, surgical instrument that detects and/or identifies range of movement of a spinal implant disposed with tissue. In some embodiments, the surgical instrument includes a tracking and/or mapping tool that identifies range of motion limits due to tissue impingement. In some embodiments, the surgical instrument has one or more image guides, which provide position and rotation indicia and/or display of a spinal implant via a camera sensor and a computer display screen. In some embodiments, the surgical system includes a surgical instrument that has two image guide arrays.

In some embodiments, the surgical instrument includes a navigation tracker that is optically tracked and requires a line-of-sight view to a sensor, such as, for example, a camera. In some embodiments, the surgical system includes a navigation tracker attached to a surgical instrument and is disposed in a direct line of sight of a sensor, which includes one or more cameras. In some embodiments, the surgical system includes an O-arm medical imaging device that digitally captures images of an anatomy. In some embodiments, the tracker communicates with a surgical navigation system to determine and/or display surgical instrument positioning relative to the anatomy.

In some embodiments, one or all of the components of the surgical system may be disposable, peel pack and/or pre packed sterile devices. One or all of the components of the surgical system may be reusable. The surgical system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

Figure 2:
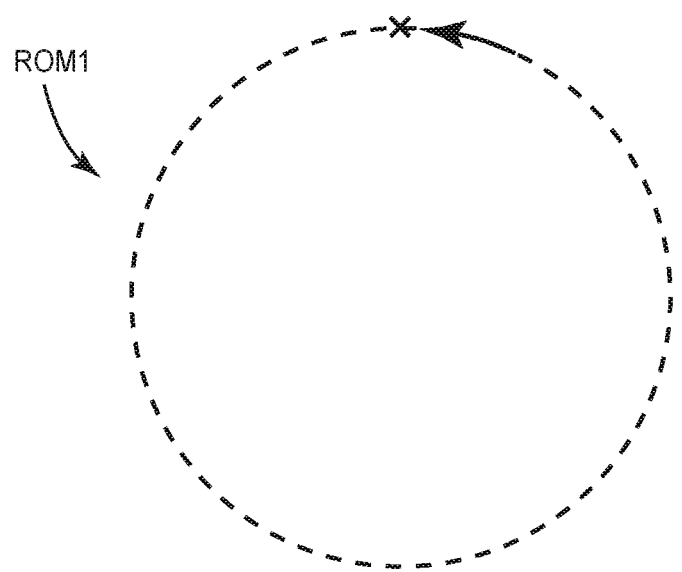
FIG. 2 is a schematic representation of movement of components of the system shown in FIG. 1.

The following discussion includes a description of a surgical system including a surgical instrument, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1 and 2, there are illustrated components of a surgical system 10.

The components of surgical system 10 can be fabricated from biologically acceptable materials suitable for medical applications, including metals, synthetic polymers and/or ceramics. For example, the components of surgical system 10, individually or collectively, can be fabricated from materials such as stainless steel alloys, aluminum, commercially pure titanium, titanium alloys, Grade 5 titanium, superelastic titanium alloys, cobalt-chrome alloys, superelastic metallic alloys (e.g., Nitinol, super elasto-plastic metals, such as GUM METAL®), ceramics, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene and/or epoxy.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Figure 5:
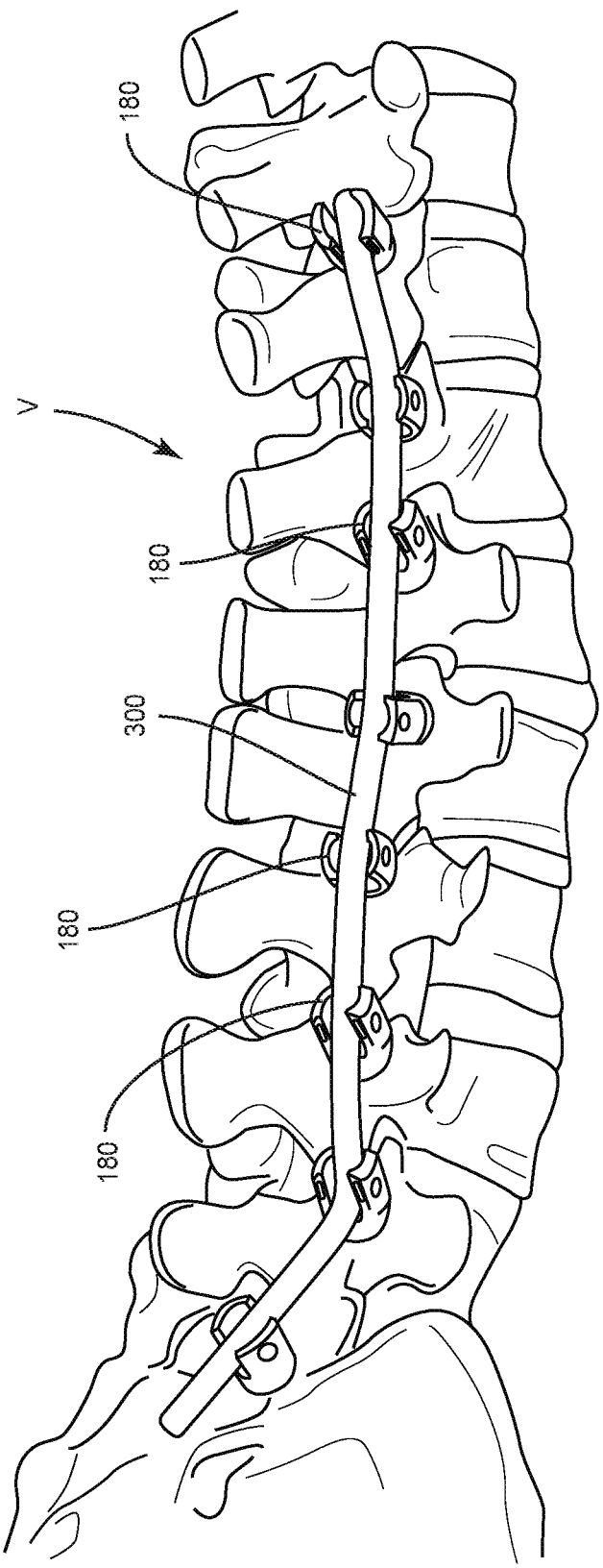
FIG. 5 is a perspective view of components one embodiment of a surgical system in accordance with the principles of the present disclosure disposed with vertebrae.

Surgical system 10 is employed, for example, with a fully open surgical procedure, a minimally invasive procedure including percutaneous techniques, and mini-open surgical techniques to customize and introduce instrumentation and/or a spinal implant, such as, for example, one or more bone fasteners at a surgical site of a patient, which includes, for example, a spine having vertebrae V, as shown in FIG. 5.

Surgical system 10 includes a spinal implant, such as, for example, a bone fastener 180. Bone fastener 180 comprises a screw shaft assembly 12 and a head assembly 13. In some embodiments, screw shaft assembly 12 and head assembly 13 are assembled in situ or prior to implant to form bone fastener 180, as described herein. Head assembly 13 includes a head, such as, for example, a receiver 14. Receiver 14 extends along and defines an axis X1. Receiver 14 includes a pair of spaced apart arms 16, 18 that define an implant cavity 20 therebetween configured for disposal of a component of a spinal construct, such as, for example, a spinal rod (not shown).

Arms 16, 18 each extend parallel to axis X1. In some embodiments, arm 16 and/or arm 18 may be disposed at alternate orientations, relative to axis X1, such as, for example, transverse, perpendicular and/or other angular orientations such as acute or obtuse, coaxial and/or may be offset or staggered. Arms 16, 18 each include an arcuate outer surface extending between a pair of side surfaces. At least one of the outer surfaces and the side surfaces of arms 16, 18 have at least one recess or cavity therein configured to receive an insertion tool, compression instrument and/or instruments for inserting and tensioning bone fastener 180. In some embodiments, arms 16, 18 are connected at proximal and distal ends thereof such that receiver 14 defines a closed spinal rod slot.

Cavity 20 is substantially U-shaped. In some embodiments, all or only a portion of cavity 20 may have alternate cross section configurations, such as, for example, closed, V-shaped, W-shaped, oval, oblong triangular, square, polygonal, irregular, uniform, non-uniform, offset, staggered, and/or tapered. In some embodiments, receiver 14 includes an inner surface having a thread form located adjacent arm 16 and a thread form located adjacent arm 18. The thread forms are each configured for engagement with a coupling member, such as, for example, a setscrew (not shown), to retain the spinal rod within cavity 20. In some embodiments, receiver 14 may include alternate configurations, such as, for example, closed, open and/or side access.

Shaft assembly 12 extends along an axis X2 between a proximal portion 22 and a distal tip 24. Shaft assembly 12 is configured for fixation with vertebrae, as described herein. Shaft assembly 12 includes a thread 26 configured for engagement with vertebrae V, as shown in FIG. 1. Thread 26 is continuous along a length of shaft assembly 12. In some embodiments, thread 26 may be intermittent, staggered, discontinuous and/or may include a single thread turn or a plurality of discrete threads. In some embodiments, other penetrating elements may be located on shaft assembly 12, such as, for example, a nail configuration, barbs, expanding elements, raised elements, ribs, and/or spikes to facilitate engagement of shaft 16 with tissue. In some embodiments, thread 26 may be self-tapping or intermittent.

Receiver 14 includes a selected movement configuration with shaft assembly 12. In some embodiments, receiver 14 is rotatable and/or pivotable relative to shaft assembly 12 in a selected range of movement configuration, as described herein. The selected range of movement can be limited due to engagement and/or impingement of receiver 14 with tissue. Such limitations of range of movement are identifiable and/or detectable with a surgical instrument 25, as described herein. In some embodiments, bone fastener 180 is configured to selectively move between an orientation in which axis X1 extends parallel to axis X2 and is coaxial with axis X2, and an orientation in which axis X1 extends transverse to axis X2. In some embodiments, receiver 14 is connectable with shaft assembly 12 to include a selected range of movement configuration such that bone fastener 180 comprises, for example, a multi-axial screw (MAS), a uni-axial screw (UAS), a sagittal adjusting screw (SAS) or a transverse sagittal adjusting screw (TSAS). In some embodiments, surgical system 10 can include one or more multi-axial screws, sagittal angulation screws, pedicle screws, mono-axial screws, uni-planar screws, facet screws, tissue penetrating screws, conventional screws, expanding screws and/or posts. In some embodiments, surgical system 10 can include one or a plurality of bone fasteners, connectors, spinal rods and/or plates, which may be employed with a single vertebral level or a plurality of vertebral levels, and/or engaged with vertebrae in various orientations, such as, for example, series, parallel, offset, staggered and/or alternate vertebral levels. In some embodiments, connection of receiver 14 with shaft assembly 12 can be actuated by a manual engagement and/or non-instrumented assembly, which may include a practitioner, surgeon and/or medical staff grasping receiver 14 and shaft assembly 12 and forcibly snap or pop fitting the components together.

Receiver 14 is connectable with surgical instrument 25. Surgical instrument 25 includes a member 28 and is configured to identify a range of movement of receiver 14 relative to shaft assembly 12 and/or a range of movement of receiver 14 relative to tissue, as described herein. Member 28 includes a handle 38 and a shaft 40. Shaft 40 is configured to connect member 28 with bone fastener 180, as described herein. Handle 38 is configured to facilitate manipulating, moving, translating and/or rotating receiver 14 relative to shaft assembly 12 to identify and/or detect range of movement data points, as described herein. Handle 38 extends between an end 42 and an end 44 that extends from shaft 40, as shown in FIG. 1. In some embodiments, handle 38 may include alternate surface configurations to enhance gripping of handle 38, such as, for example, rough, arcuate, undulating, mesh, porous, semi-porous, dimpled and/or textured. In some embodiments, handle 38 may include alternate cross section configurations, such as, for example, oval, oblong, triangular, square, hexagonal, polygonal, irregular, uniform, non-uniform and/or tapered. In some embodiments, handle 38 may be assembled with shaft 40, as described herein. In some embodiments, handle 38 may be monolithically formed with shaft 40. In some embodiments, handle 38 may be disposed at alternate orientations relative to shaft 40, such as, for example, transverse, parallel, perpendicular and/or other angular orientations such as acute or obtuse, co-axial, offset, and/or staggered.

Shaft 40 is configured for connection with receiver 14 such that member 28 can be fixed with receiver 14 to allow member 28 to move with receiver 14. For example, as receiver 14 rotates or pivots relative to shaft assembly 12, member 28 rotates or pivots relative to shaft assembly 12. Receiver 14 and member 28 are configured to rotate about axis X2 relative to shaft assembly 12, in the directions shown by arrows A and B in FIG. 1, as provided by the selected movement configuration of a bone fastener 180. In some embodiments, an outer surface of shaft 40 is threaded and configured to mate with the thread forms of arms 16, 18 to facilitate engagement of member 28 with receiver 14. A threaded engagement of member 28 with receiver 14, for example a clockwise rotation of shaft 40 relative to receiver 14, fixes receiver 14 with member 28 such that shaft 40 is oriented to apply a force to receiver 14. This force fixes a position of shaft 40 relative to receiver 14 and/or forms a mating engagement between member 28 and bone fastener 180. This configuration resists and/or prevents movement and/or rotation of member 28 relative to receiver 14.

To release member 28 from receiver 14, member 28 is disengaged from receiver 14, for example a counter-clockwise rotation of shaft 40 relative to receiver 14, to release member 28 from receiver 14. In some embodiments, member 28 can be variously connected with receiver 14, such as, for example, via an integral connection, friction fit, pressure fit, interlocking engagement, dovetail connection, clips, barbs, tongue in groove, threaded, magnetic, key/keyslot and/or drill chuck.

Bone fastener 180, as described herein, includes receiver 14, which is configured for rotation relative to shaft assembly 12 in a selected range of movement configuration ROM1. In some embodiments, a selected range of movement configuration ROM1 of receiver 14 relative to shaft assembly 12 includes a MAS configuration. The MAS configuration of receiver 14 relative to shaft assembly 12 includes a selected range of movement configuration ROM1 having movement of receiver 14 in one or a plurality of axial orientations relative to shaft assembly 12. As such, receiver 14 is rotatable along a path x through an angle of 360 degrees about axis X2 to define a perimeter and/or circumference corresponding to ROM1, as shown in FIG. 2, and includes relative rotation along the one or a plurality of axial orientations relative to shaft assembly 12.

Figure 3:
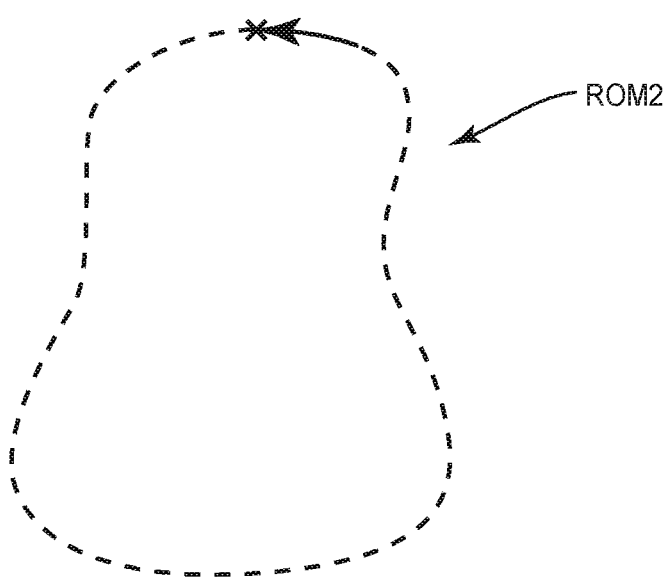
FIG. 3 is a schematic representation of movement of components of the system shown in FIG. 1.

In some embodiments, upon disposal of bone fastener 180 with tissue, the ROM1 of receiver 14 relative to shaft assembly 12 can be limited and/or restricted due to engagement and/or impingement of receiver 14 by patient anatomy. For example, upon disposal of bone fastener 180 with tissue such that shaft assembly 12 penetrates tissue and an outer surface of receiver 14 is disposed adjacent the tissue, the actual flexibility and/or movement of receiver 14 relative to shaft assembly 12 can be limited and/or impinged. Such engagement and/or impingement of receiver 14 limits and/or restricts the MAS configuration of ROM1 and the actual movement of receiver 14 relative to shaft assembly 12 includes a limited and/or restricted range of movement ROM2. As such, receiver 14 is rotatable along a path xx through an angle of 360 degrees about axis X2 to define a limited and/or restricted perimeter and/or circumference corresponding to ROM2, as shown in FIG. 3, and includes a limited and/or restricted rotation along the one or a plurality of axial orientations relative to shaft assembly 12. ROM2 includes a limited and/or restricted range of movement of receiver 14 relative to shaft assembly 12 and/or tissue to which shaft assembly 12 is disposed that is limited due to impingement of receiver 14 by tissue. Path xx of receiver 14 is determined at least in part by the location of bone or other tissue relative to an outer surface of receiver 14.

Member 28 tracks and/or maps the actual range of movement ROM2 when bone fastener 180 is implanted with tissue. In some embodiments, receiver 14 is manipulated by member 28 in a selected motion, such as, for example, a sweeping rotational motion to identify and/or detect tissue impingement of ROM1 to provide ROM2. In some embodiments, data points identified and/or detected by surgical instrument 25 include range of movement ROM2, which are transmitted to a computer 220, which includes spinal rod bending software to determine a selected rod configuration and communicates commands to an automated rod bending device, as described herein. In some embodiments, surgical instrument 25 identifies and/or detects such data points to provide actual flexibility of each receiver 14 to optimize a fixation rod path between bone fasteners 180 during automated rod bending, as described herein.

In some embodiments, surgical instrument 25 includes an image guide, such as, for example, a navigation component 30 connected with member 28. Navigation component 30 is configured to generate a signal representative of a position of receiver 14 and/or axis X1 relative to shaft assembly 12, axis X2 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, navigation component 30 is connected with member 28 via an integral connection, friction fit, pressure fit, interlocking engagement, mating engagement, dovetail connection, clips, barbs, tongue in groove, threaded, magnetic, key/keyslot and/or drill chuck.

Figure 4:
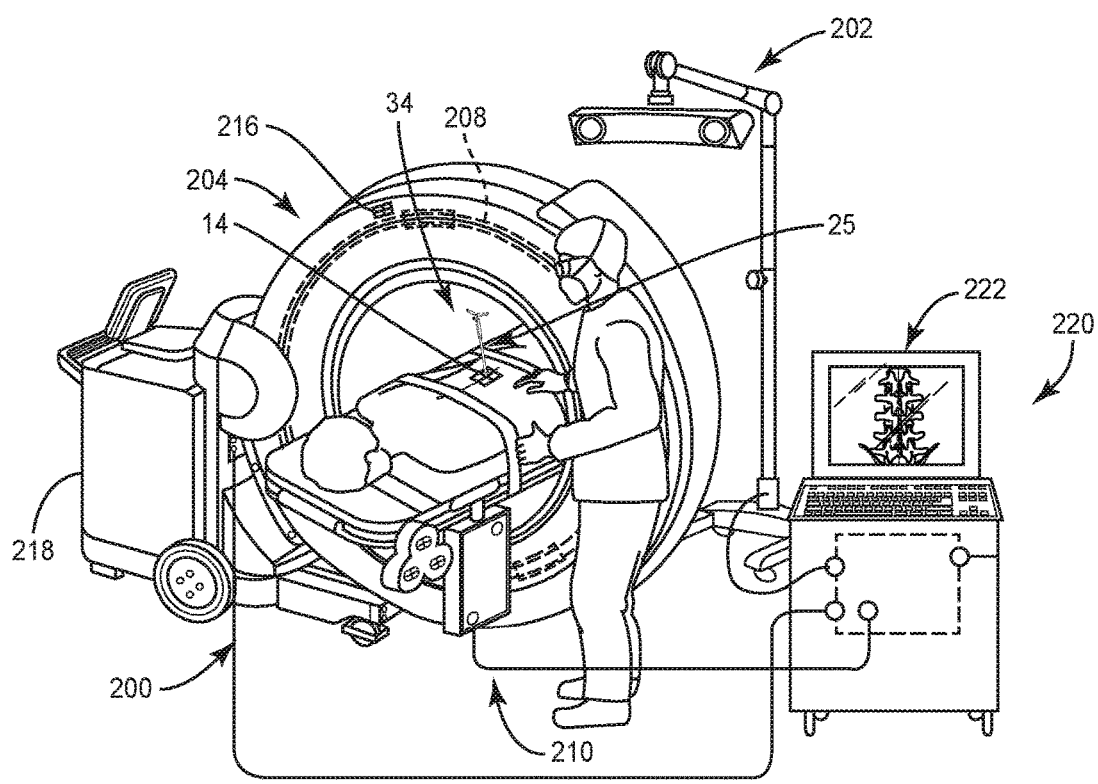
FIG. 4 is a perspective view of components one embodiment of a surgical system in accordance with the principles of the present disclosure.

Navigation component 30 includes an emitter array 34. Emitter array 34 is configured for generating a signal to a sensor array 202 of a surgical navigation system 200, as shown in FIG. 4 and described herein, representing the range of movement of receiver 14 relative to shaft assembly 12, for example ROM2, and/or a position or a trajectory of receiver 14 relative to shaft assembly 12 and/or tissue for display on a monitor 222.

In some embodiments, the signal generated by emitter array 34 represents proximity of an outer surface of receiver 14 relative to tissue, such as, for example, bone. In some embodiments, the signal generated by emitter array 34 represents an actual range of movement of receiver 14 relative to shaft assembly 12 and/or tissue. In some embodiments, the signal generated by emitter array 34 represents a three dimensional position of bone fastener 180 relative to tissue. In some embodiments, the signal generated by emitter array 34 represents tissue impingement on receiver 14 that limits the range of movement of receiver 14 relative to shaft assembly 12 and/or tissue. In some embodiments, the signal generated by emitter array 34 represents data points of bony impingement of receiver 14 with tissue.

In some embodiments, sensor array 202 receives signals from emitter array 34 to provide a three-dimensional spatial position and/or a trajectory of receiver 14 and/or axis X1 relative to shaft assembly 12, axis X2 and/or tissue. Emitter array 34 communicates with a processor of computer 220 of navigation system 200 to generate data for display of an image on monitor 222, as described herein. In some embodiments, sensor array 202 receives signals from emitter array 34 to provide a visual representation of range of movement ROM2 and/or an angular position of receiver 14 and/or axis X1 relative to shaft assembly 12, axis X2 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 200 is configured for acquiring and displaying medical imaging, such as, for example, x-ray images appropriate for a given surgical procedure. In some embodiments, pre-acquired images of a patient are collected. In some embodiments, surgical navigation system 200 can include an O-Arm® imaging device 204 sold by Medtronic Navigation, Inc. having a place of business in Louisville, Colo., USA. Imaging device 204 may have a generally annular gantry housing that encloses an image capturing portion 208.

In some embodiments, navigation system 200 comprises an image capturing portion 208 that may include an x-ray source or emission portion and an x-ray receiving or image receiving portion located generally or as practically possible 180 degrees from each other and mounted on a rotor (not shown) relative to a track of image capturing portion 208. Image capturing portion 208 can be operable to rotate 360 degrees during image acquisition. Image capturing portion 208 may rotate around a central point or axis, allowing image data of the patient to be acquired from multiple directions or in multiple planes. Surgical navigation system 200 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 200 can include C-arm fluoroscopic imaging systems, which can generate three-dimensional views of a patient. The position of image capturing portion 208 can be precisely known relative to any other portion of an imaging device 204 of navigation system 200. In some embodiments, a precise knowledge of the position of image capturing portion 208 can be used in conjunction with a tracking system 210 to determine the position of image capturing portion 208 and the image data relative to the patient.

Tracking system 210 can include various portions that are associated or included with surgical navigation system 200. In some embodiments, tracking system 210 can also include a plurality of types of tracking systems, such as, for example, an optical tracking system that includes an optical localizer, such as, for example, sensor array 202 and/or an EM tracking system that can include an EM localizer. Various tracking devices can be tracked with tracking system 210 and the information can be used by surgical navigation system 200 to allow for a display of a position of an item, such as, for example, a patient tracking device, an imaging device tracking device 216, and an instrument tracking device, such as, for example, emitter array 34, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to a computer 218 where they may be forwarded to computer 220. Image transfer may be performed over a standard video connection or a digital link including wired and wireless. Computer 220 provides the ability to display, via monitor 222, as well as save, digitally manipulate, or print a hard copy of the received images. In some embodiments, images may also be displayed to the surgeon through a heads-up display.

In some embodiments, surgical navigation system 200 provides for real-time tracking of bone fastener 180 such that ROM1, ROM2, the position of receiver 14 relative to shaft assembly 12 and/or tissue can be tracked. In some embodiments, real-time tracking of the position of receiver 14 relative to shaft assembly 12 and/or tissue can be limited due to impingement of receiver 14 with tissue, wherein such limitations of range of movement, for example ROM2 are identifiable and/or detectable with surgical instrument 25, as described herein. Sensor array 202 is located in such a manner to provide a clear line of sight with emitter array 34, as described herein. In some embodiments, fiducial markers 32 of emitter array 34 communicate with sensor array 202 via infrared technology. Sensor array 202 is coupled to computer 220, which may be programmed with software modules that analyze signals transmitted by sensor array 202 to determine the position of each object in a detector space.

In some embodiments, sensor array 202 communicates with computer 220 to transmit range of movement data of receiver 14 relative to shaft assembly 12, as described herein. In some embodiments, the processor sends such information to monitor 222, which provides a visual representation of the range of movement of receiver 14 relative to shaft assembly 12. For example, range of movement ROM2 of receiver 14 relative to shaft assembly 12 may affect the contouring of a spinal rod that is configured to be positioned within implant cavities 20 of bone fasteners 180 to correct a spinal deformity. In some embodiments, the spinal correction and/or rod bending software can be employed to determine the shape of the spinal rod, based at least in part upon the range of movement of receiver 14 relative to shaft assembly 12, as described herein, such that surgical instrument 25 identifies and/or detects ROM2 data points to provide actual flexibility of each receiver 14 to optimize a fixation rod path between bone fasteners 180 during automated rod bending, as described herein. In some embodiments, the software is utilized to determine a selected spinal correction and the corresponding shape and/or contour of the spinal rod to fit within implant cavities 20 of bone fasteners 180 by rotating receivers 14 relative to shaft assembly 12 within range of movement ROM2, as described herein.

In assembly, operation and use, surgical system 10, similar to the systems and methods described herein, is employed with a surgical procedure for treatment of a spinal disorder affecting a section of a spine of a patient, as discussed herein. For example, the components of surgical system 10 can be used with a surgical procedure for treatment of a condition or injury of an affected section of the spine including vertebrae V, as shown in FIG. 5. In some embodiments, one or all of the components of surgical system 10 can be delivered or implanted as a pre-assembled device or can be assembled in situ. Surgical system 10 may be completely or partially revised, removed or replaced.

The components of surgical system 10 can be employed with a surgical treatment of an applicable condition or injury of an affected section of a spinal column and adjacent areas within a body, such as, for example, vertebrae V. In some embodiments, the components of surgical system 10 may be employed with one or a plurality of vertebra. To treat a selected section of vertebrae V, a medical practitioner obtains access to a surgical site including vertebrae V in any appropriate manner, such as through incision and retraction of tissues. In some embodiments, the components of surgical system 10 can be used in any existing surgical method or technique including open surgery, mini-open surgery, minimally invasive surgery and percutaneous surgical implantation, whereby vertebrae V are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of surgical system 10 including bone fasteners 180, as described herein, adjacent an area within the patient's body, such as, for example, vertebrae V. In some embodiments, a preparation instrument (not shown) can be employed to prepare tissue surfaces of vertebrae V, as well as for aspiration and irrigation of a surgical region.

Pilot holes are made in vertebrae V in a selected orientation. Bone fasteners 180 are each engaged with a driver. Each receiver 14 of the bone fasteners 180 to be attached with the tissue of vertebrae V includes a selected range of movement configuration ROM1. For example, an MAS bone fastener 180 includes a receiver 14 having a ROM1 relative to shaft assembly 12, as shown in FIG. 2, and is rotatable along path x through an angle of 360 degrees about axis X2 to define a perimeter and/or circumference corresponding to ROM1. Bone fasteners 180 are each aligned with one of the pilot holes and the drivers are rotated, torqued, inserted or otherwise connected with bone fasteners 180 such that bone fasteners 180 each translate axially within one of the pilot holes for engagement and fixation with the tissue of vertebrae V. In some embodiments, at least one of bone fasteners 180 includes a MAS or a SAS movement configuration.

Surgical instrument 25 is connected with each bone fastener 180 to identify a range of movement of receiver 14 relative to shaft assembly 12 and/or a range of movement of receiver 14 relative to tissue, as described herein. Shaft 40 is connected with each receiver 14 such that member 28 can be fixed with receiver 14 to allow member 28 to move with receiver 14. As receiver 14 rotates or pivots relative to shaft assembly 12, member 28 rotates or pivots relative to shaft assembly 12.

Member 28 is engaged with the receiver 14 of each bone fastener 180 disposed with vertebrae V to track and/or map the actual range of movement ROM2 of each receiver 14 of the bone fasteners 180 implanted with vertebrae V. Bone fasteners 180 are disposed with vertebrae V such that an outer surface of receiver 14 is disposed adjacent bone and the actual flexibility and/or movement of receiver 14 relative to shaft assembly 12 can be limited and/or impinged. Such engagement and/or impingement of receiver 14 with tissue limits and/or restricts the ROM1 of bone fastener 180 and the actual movement of receiver 14 relative to shaft assembly 12 includes a limited and/or restricted range of movement ROM2. As such, receiver 14 is rotatable along a path xx through an angle of 360 degrees about axis X2 to define a limited and/or restricted perimeter and/or circumference corresponding to ROM2, as shown in FIG. 3, and includes a limited and/or restricted rotation along the one or a plurality of axial orientations relative to shaft assembly 12. Each receiver 14 is manipulated with member 28 in a sweeping rotational motion to identify and/or detect tissue impingement of ROM1 to provide ROM2 such that surgical instrument 25 identifies and/or detects ROM2 data points to provide actual flexibility of each receiver 14 to optimize a fixation rod path between bone fasteners 180 during automated rod bending, as described herein. Data points identified and/or detected by surgical instrument 25 include range of movement ROM2, which are transmitted to computer 220, which includes spinal rod bending software to determine a selected rod configuration and communicates commands to an automated rod bending device, as described herein. In some embodiments, surgical instrument 25 is employed to identify and/or detect ROM2 data points of alternate movement configurations of a bone fastener, as described herein, for transmission to computer 220.

Sensor array 202 receives signals from emitter array 34 to provide a three-dimensional spatial position and/or a trajectory of receiver 14, as described herein. Emitter array 34 communicates with the processor of computer 220 of navigation system 200 to generate ROM2 data points for display from monitor 222. In some embodiments, this procedure is repeated for each of bone fasteners 180.

The identified and/or mapped range of movement ROM2 includes data points that are employed with a selected rod contour, spinal rod template configuration and/or selected spinal correction treatment to calculate a selected spinal rod configuration for disposal with one or more of bone fasteners 180. The data points are communicated to the software of computer 220, as described herein, and based on such data points, computer 220 generates three dimensional coordinates of the shape of a spinal rod 300 to be implanted with vertebrae V. Computer 220 communicates a corresponding signal and/or commands to an automated implant bending device, which may be disposed within a sterile field, to contour spinal rod 300. See, for example, the disclosure of automated implant bending devices, systems and methods shown and described in commonly owned and assigned U.S. patent application Ser. No. 15/479,051 filed Apr. 4, 2017; the disclosure of automated implant bending devices, systems and methods shown and described in commonly owned and assigned U.S. patent application Ser. No. 15/479,585 filed Apr. 5, 2017; the disclosure of automated implant bending devices, systems and methods shown and described in commonly owned and assigned U.S. patent application Ser. No. 15/480,002 filed Apr. 5, 2017; and the disclosure of automated implant bending devices, systems and methods shown and described in commonly owned and assigned U.S. patent application Ser. No. 15/480,123 filed Apr. 5, 2017, the entire contents of each of these disclosures being incorporated herein by reference.

In some embodiments, computer 220 generates three dimensional coordinates of the shape of spinal rod 300, which may be determined from intra-operative fluoroscopy with bone fasteners 180 installed. In some embodiments, fluoroscopic images taken are transmitted to computer 220. Image transfer may be performed over a standard video connection or a digital link including wired and wireless. Computer 220 and/or the graphical interface, as described herein, provides the ability to display, via monitor 222, as well as save, digitally manipulate, or print a hard copy of the received images. In some embodiments, images may also be displayed to the surgeon through a heads-up display.

In some embodiments, a graphical interface including monitor 222, as described herein, provides three dimensional graphical representation of spinal rod 300 formation. In some embodiments, the implant bending device (not shown) communicates with computer 220 and/or the graphical interface to provide the curvature coordinates of spinal rod 300, which may include a geometric angle between two consecutive points on spinal rod 300. In some embodiments, the software of computer 220 determines how to manipulate each of receivers 14 relative to shaft assemblies 12 within selected range of movement configuration ROM2 such that spinal rod 300 can be positioned within implant cavities 20 to correct and/or treat a condition or injury of vertebrae V.

In some embodiments, surgical system 10 includes an agent, which may be disposed, packed or layered within, on or about the components and/or surfaces of surgical system 10. In some embodiments, the agent may include bone growth promoting material, such as, for example, bone graft to enhance fixation with vertebrae V. The components of surgical system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implanted components of surgical system 10 are removed from the surgical site and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a member including a handle and a shank coupled to the handle, the shank defining a longitudinal axis, the shank being connectable with a head of a bone fastener having a shaft attachable with tissue, the shank and the head being movable relative to the shaft in a plurality of axial orientations to define a perimeter and/or circumference corresponding to a range of movement of the head relative to the shaft; and
an image guide connected with the handle by a rod that is coaxial with the longitudinal axis, the image guide comprising a plurality of spaced apart emitters each extending from a surface of the image guide that extends transverse to the longitudinal axis such that the emitters are positioned radially about the longitudinal axis, the emitters being oriented relative to a sensor to communicate a signal representative of the range of movement.

2. A surgical instrument as recited in claim 1, wherein the head includes a selected movement configuration relative to the shaft and is engageable with tissue to limit the range of movement.

3. A surgical instrument as recited in claim 1, wherein the head is rotatable relative to the shaft and the member identifies an angular range of movement of the head relative to tissue.

4. A surgical instrument as recited in claim 1, wherein the signal represents tissue impingement on the head that limits the range of movement.

5. A surgical instrument as recited in claim 1, wherein the signal represents proximity of an outer surface of the head relative to tissue.

6. A surgical instrument as recited in claim 1, wherein the head includes a selected movement configuration relative to the shaft and the signal represents an actual range of movement of the head relative to tissue.

7. A surgical instrument as recited in claim 1, wherein the signal represents data points of bony impingement of the head with tissue.

8. A surgical instrument as recited in claim 1, wherein the head includes a receiver that defines a rod cavity and the receiver comprises a multi-axial movement configuration.

9. A surgical instrument as recited in claim 1, wherein the head includes a receiver that defines a rod cavity and the receiver comprises a sagittal adjustable movement configuration.

10. A surgical instrument as recited in claim 1, wherein the signal represents a three dimensional position of the bone fastener attached with bone.

11. A surgical instrument as recited in claim 1, wherein the emitters each extend outwardly from the surface of the image guide such that the emitters each extend parallel to the longitudinal axis.

12. A surgical instrument as recited in claim 1, wherein the image guide is oriented relative to the sensor to communicate the signal and the sensor communicates with a processor to generate data for display of an image from a monitor, the image representing position of the bone fastener relative to tissue.

13. A method for treating a spine, the method comprising the steps of:
engaging a shank of a surgical instrument with a head of at least one bone fastener having a shaft attached with tissue, the shank defining a longitudinal axis; and
moving the surgical instrument and the head relative to the shaft in a plurality of axial orientations to define a perimeter and/or circumference corresponding to a range of movement of the head relative to the shaft, the surgical instrument including a handle coupled to the shank and an image guide coupled to the handle by a rod that is coaxial with the longitudinal axis, the image guide comprising a plurality of spaced apart emitters each extending from a surface of the image guide that extends transverse to the longitudinal axis such that the emitters are positioned radially about the longitudinal axis, the emitters being oriented relative to a sensor to communicate a signal representative of the range of movement.

14. A method as recited in claim 13, further comprising the step of communicating the signal with a processor to generate data for display of an image from a monitor, the image representing position of the at least one bone fastener relative to tissue.

15. A method as recited in claim 13, wherein the at least one bone fastener includes a plurality of bone fasteners attached with tissue and further comprising the step of disposing a spinal rod with the bone fasteners.

16. A surgical system comprising:
   at least one bone fastener including a head and a shaft attachable with tissue, the head including a selected movement configuration relative to the shaft;
   a surgical instrument including a handle and a shank coupled to the handle, the shank defining a longitudinal axis, the shank comprising a threaded outer surface configured to engage a threaded inner surface of the head to connect the shank with the head, the head and the shank being movable relative to the shaft in a plurality of axial orientations to define a perimeter and/or circumference corresponding to a range of movement of the head relative to the shaft, the surgical instrument including an image guide having a base, the surgical instrument comprising a rod extending between opposite first and second ends that are each coaxial with the longitudinal axis, the first end of the rod directly engaging the handle, the second end of the rod directly engaging a bottom surface of the base, the image guide comprising a plurality of spaced apart emitters each extending from a top surface of the base such that the emitters are positioned radially about the longitudinal axis, the top and bottom surfaces of the base each extending perpendicular to the longitudinal axis, the emitters being oriented relative to a sensor to communicate a signal representative of the range of movement; and
   a tracking device including the sensor that receives the signal and communicates with a processor to generate data for display of an image from a monitor, the image representing position of the at least one bone fastener relative to the tissue.

17. A surgical system as recited in claim 16, wherein the signal represents tissue impingement on the head that limits the range of movement.

18. A surgical system as recited in claim 16, wherein the signal represents proximity of an outer surface of the head relative to tissue.

19. A surgical system as recited in claim 16, wherein the image guide comprises one or a plurality of emitters mounted with the surgical instrument.

20. A surgical system as recited in claim 16, wherein the at least one bone fastener includes a plurality of bone fasteners attached with tissue and further comprising a spinal rod disposable with the bone fasteners.

* * * * *